United States Patent
Kinnunen et al.

(10) Patent No.: US 8,021,312 B2
(45) Date of Patent: Sep. 20, 2011

(54) ARRANGEMENT, METHOD AND COMPUTER PROGRAM FOR DETERMINING PHYSICAL ACTIVITY LEVEL OF HUMAN BEING

(75) Inventors: Hannu Kinnunen, Oulu (FI); Jari Miettinen, Oulu (FI)

(73) Assignee: Polar Electro Oy, Kempele (FI)

( * ) Notice: Subject to any disclaimer, the term of this patent is extended or adjusted under 35 U.S.C. 154(b) by 752 days.

(21) Appl. No.: 10/980,614

(22) Filed: Nov. 3, 2004

(65) Prior Publication Data

US 2005/0130802 A1 Jun. 16, 2005

(30) Foreign Application Priority Data

Nov. 21, 2003 (FI) ..................... 20031699

(51) Int. Cl.
*A61B 5/11* (2006.01)
*A63B 71/00* (2006.01)
*G01C 22/00* (2006.01)
*G01C 22/02* (2006.01)

(52) U.S. Cl. ....... 600/595; 235/105; 377/24.2; 702/160; 482/8

(58) Field of Classification Search .............. 600/595; 235/105; 377/24.2; 702/160; 482/8, 9
See application file for complete search history.

(56) References Cited

U.S. PATENT DOCUMENTS

| | | | |
|---|---|---|---|
| 4,625,733 A | | 12/1986 | Saynajakangas |
| 4,962,469 A | * | 10/1990 | Ono et al. ............. 377/24.2 |
| 5,164,967 A | * | 11/1992 | Endo et al. ............. 377/24.2 |
| 5,573,013 A | | 11/1996 | Conlan |
| 6,477,421 B1 | | 11/2002 | Andersen et al. |
| 2002/0109600 A1 | * | 8/2002 | Mault et al. ............. 340/573.1 |
| 2004/0112151 A1 | | 6/2004 | Maxwell et al. |
| 2004/0116837 A1 | * | 6/2004 | Yamaguchi et al. ....... 600/595 |
| 2005/0004436 A1 | | 1/2005 | Nissila et al. |

FOREIGN PATENT DOCUMENTS

| | | |
|---|---|---|
| EP | 0816986 | 1/1998 |
| EP | 1366712 A1 | 12/2003 |
| EP | 1473655 A1 | 11/2004 |
| JP | 03037516 A | 2/1991 |
| JP | 04192095 A | 7/1992 |
| JP | 10-113343 | 5/1998 |
| JP | 11-042220 | 2/1999 |

(Continued)

OTHER PUBLICATIONS

IDEEA Overview, "Overview of IDEEA Device", <http://web.archive.org/web/20030830141758/http://www.minisun.com/IDDA_overview.asp> (2003).

(Continued)

*Primary Examiner* — Max Hlndenburg
*Assistant Examiner* — Emily Lloyd
(74) *Attorney, Agent, or Firm* — Hoffmann & Baron, LLP

(57) ABSTRACT

An arrangement, method and computer program for determining the physical activity level of a human being. The arrangement comprises a movement sensor to be attached to an upper limb of the human being for measuring upper limb movements, a processing unit connected to the movement sensor for filtering upper limb movements following one another more frequently than a predetermined threshold period from upper limb movements during a determination period, for forming the number of upper limb movements during the determination period from the filtered upper limb movements during the determination period, and for determining the physical activity level on the basis of the number of upper limb movements during the determination period formed from the filtered upper limb movements during the determination period.

25 Claims, 5 Drawing Sheets

FOREIGN PATENT DOCUMENTS

| | | |
|---|---|---|
| JP | 2000093409 A | 4/2000 |
| JP | 2002-263086 | 9/2002 |
| JP | 3091922 | 11/2002 |
| JP | 2002-360549 | 12/2002 |
| JP | 2003123051 A | 4/2003 |
| JP | 08077322 A | 5/2011 |
| WO | WO2004/052202 A1 | 6/2004 |

OTHER PUBLICATIONS

Official Action issued concerning corresponding Finnish priority application No. 20031699.

Daniel D. Redmond and Frederick W. Hegge, "Observations on the Design and Specification of a Wrist-Worn Human Activity Monitoring System", *Behavior Research Methods, Instruments, & Computers*, vol. 17, No. 6, pp. 659-669 (1985).

Warren W. Tryon and Robert Williams, "Fully Proportional Actigraphy: A New Instrument", *Behavior Research Methods, Instruments, & Computers*, vol. 28, No. 3, pp. 392-403 (1996).

Kazushige Ouchi, Takuji Suzuki and Miwako Doi, "Lifeminder: A Wearable Healthcare Support System Using User's Context", *Proceedings of the 22$^{nd}$ International IEEE Conference on Distributed Computing Systems Workshops*, pp. 1-2 (2002).

Peter H. Veltink, Hans B.J. Bussmann, Wiebe de Vries, Wim L.J. Martens and Rob C. Van Lummel, "Detection of Static and Dynamic Activities Using Uniaxial Accelerometers", *IEEE Transactions on Rehabilitation Engineering*, vol. 4, No. 4, pp. 375-385 (1996).

European Search Report, European Application No. EP 04105445.

Eus J. W. van Someran, "Actigraphic Monitoring of Movement and Rest-Activity Rhythms in Aging, Alzheimer's Disease, and Parkinson's Disease", *IEEE Transactions on Rehabilitation Engineering*, vol. 5, No. 4, pp. 394-398 (1997).

Eus J. W. van Someran et al., "A New Actigraph for Long-Term Registration of the Duration and Intensity of Tremor and Movement", *IEEE Transactions on Biomedical Engineering*, vol. 45, No. 3, pp. 386-395 (1998).

Wikipedia, The Free Encyclopedia, "USB Flash Drive", http://wikipedia.org/wiki/USB_flash_drive, pp. 1-17 (Jun. 18, 2010).

Japanese Office Action concerning corresponding Japanese Application 2006-136307 with English translation.

* cited by examiner

ARRANGEMENT, METHOD AND COMPUTER PROGRAM FOR DETERMINING PHYSICAL ACTIVITY LEVEL OF HUMAN BEING

CROSS-REFERENCE TO RELATED APPLICATION

This application claims priority based on Finnish Patent Application No. 20031699, filed on Nov. 21, 2003, which is incorporated herein by reference.

FIELD OF THE INVENTION

The invention relates to an arrangement for determining the physical activity level of a human being, a method of determining the physical activity level of a human being, and to a computer program distribution medium, which is readable by a data processing device and which encodes computer program commands to enable the running of a computer process which determines the physical activity level of a human being.

BRIEF DESCRIPTION OF THE RELATED ART

Various ways exist for determining the physical activity level of a human being, for example methods based on the use of water containing certain isotopes (known as "doubly labeled water"), on calorimetry and on monitoring oxygen intake, heart rate and body temperature. The three first mentioned methods are expensive and/or difficult and thus not suitable for use by consumers. The method based on heart rate monitoring may be inaccurate at very low or high activity levels. The method based on monitoring the body temperature requires strictly controlled conditions.

Wrist-worn measuring devices provided with an acceleration sensor are more suitable for use by consumers. The acceleration sensor measures the number of hand movements as a function of time, from which the current stress level is determined. Due to the manner of measurement, this method is sensitive to recognizing hand movements but insensitive to recognizing the effect of lower limbs on energy consumption.

Since most people spend a greater part of their working time and leisure time sitting, it is advantageous to set the measuring direction on the wrist and to adjust the sensitivity to movement recognition so that the measuring device is sufficiently sensitive to recognizing and distinguishing very low activity levels.

Work and leisure also include activities involving moving, most commonly walking, when the level of energy consumption is considerably higher than in activities performed sitting or standing. Thus the measuring device has to be dimensioned to take the additional energy consumption resulting from lower limb work into account at high activity levels.

A problem is constituted by the fact that after the implementation of the previous points, the measuring device overestimates energy consumption in the case of activities which stress upper limbs but involve only a small amount of movement. Examples of such activities include cleaning, loading of a dishwasher, packing, car washing and varieties of garden work.

SUMMARY OF THE INVENTION

The object of the invention is to provide an improved arrangement for determining the physical activity level of a human being, an improved method of determining the physical activity level of a human being, and an improved computer program for determining the physical activity level of a human being.

One aspect of the invention provides an arrangement for determining the physical activity level of a human being, the arrangement comprising a movement sensor attached to an upper limb of the human being for measuring upper limb movements. The arrangement also comprises a processing unit connected to the movement sensor for filtering upper limb movements following one another more frequently than a predetermined threshold period from upper limb movements during a determination period, for forming the number of upper limb movements during the determination period from the filtered upper limb movements during the determination period, and for determining the physical activity level on the basis of the number of upper limb movements during the determination period formed from the filtered upper limb movements during the determination period.

One aspect of the invention provides a method of determining the physical activity level of a human being, the method comprising: measuring upper limb movements of the human being. The method further comprises: filtering upper limb movements following one another more frequently than a predetermined threshold period from the upper limb movements during a determination period; forming the number of upper limb movements during the determination period from the filtered upper limb movements during the determination period; and determining the physical activity level on the basis of the number of upper limb movements during the determination period formed from the filtered upper limb movements during the determination period.

One aspect of the invention provides an arrangement for determining the physical activity level of a human being, the arrangement comprising measuring means to be attached to an upper limb of the human being for measuring upper limb movements. The arrangement further comprises processing means for filtering upper limb movements following one another more frequently than a predetermined threshold period from upper limb movements during a determination period, for forming the number of upper limb movements during the determination period from the filtered upper limb movements, and for determining the physical activity level on the basis of the number of upper limb movements during the determination period formed from the filtered upper limb movements during the determination period.

One aspect of the invention provides a computer program distribution medium, which is readable by a data processing device and encodes computer program commands to enable the running of a computer process which determines the physical activity level, the process comprising: receiving measured upper limb movements of the human being. The method further comprises: filtering upper limb movements following one another more frequently than a predetermined threshold period from upper limb movements during a determination period; forming the number of upper limb movements during the determination period from the filtered upper limb movements during the determination period; and determining the physical activity level on the basis of the number of upper limb movements during the determination period formed from the filtered upper limb movements during the determination period.

The invention provides several advantages. One-dimensional measurement of movement is sufficient for measuring daily energy consumption or physical activity since the processing according to the invention minimizes the influence of the sensor's measurement direction. The sensor can be mounted towards various directions, which provides mechanical, anatomical or aesthetical advantages in accordance with a desired solution. The determination of the physical activity level according to the invention can be provided with a very good resolution capability in the case of activities for which people spend most of their time, yet maintaining the ability to distinguish activities involving movement from activities not involving movement.

BRIEF DESCRIPTION OF THE DRAWINGS

The invention will now be described in greater detail by means of preferred embodiments, with reference to the accompanying drawings, in which.

DETAILED DESCRIPTION OF THE PREFERRED EMBODIMENTS

Figure 1A:
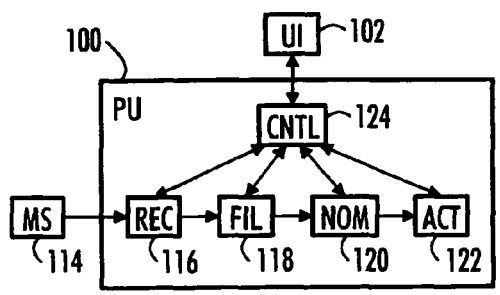
FIG. 1A is a simplified block diagram illustrating an arrangement for determining the physical activity level of a human being.

FIG. 1A illustrates an arrangement for determining the physical activity level of a human being. The arrangement comprises a movement sensor 114 to be attached to an upper limb of the human being for measuring upper limb movements. Furthermore, the arrangement comprises a processing unit 100 connected to the movement sensor 114 for processing the measured upper limb movements.

The processing unit 100 comprises processing blocks 116, 118, 120, 122, 124 for processing signals received from the movement sensor. The processing block 116 receives the movements measured by the movement sensor 114. The processing block 124 monitors and controls the operation of the other processing blocks 116, 118, 120, 122 and provides an interface through which a block external to the arrangement receives information on the determined physical activity level. In the embodiment of FIG. 1A, the arrangement comprises a user interface 102 which is connected to the interface and through which the user may view the information related to the determination. The interface can also be implemented otherwise, for example by using a file, a detachable memory, a wireless or a fixed data transmission connection or another prior art manner for transmitting information between two blocks of an electronic device.

The processing block 118 of the processing unit 100 filters upper limb movements following one another more frequently than a predetermined threshold period from upper limb movements during a determination period. In an embodiment, this is implemented such that the processing unit 100 rejects movements following each accepted upper limb movement and measured during the predetermined threshold period. Then the processing block 120 of the processing unit 100 forms the number of upper limb movements during the determination period from the filtered upper limb movements. Finally, the processing block 122 of the processing unit 100 determines the physical activity level on the basis of the number of upper limb movements during the determination period formed from the filtered upper limb movements during the determination period.

Figure 1B:
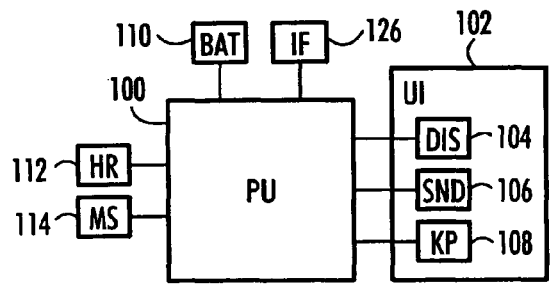
FIG. 1B is a simplified block diagram illustrating how the arrangement is mounted in a measuring device.
Figure 3:
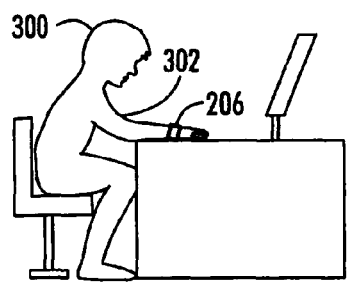
FIG. 3 illustrates determination of the physical activity level in the case of sitting.
Figure 4:
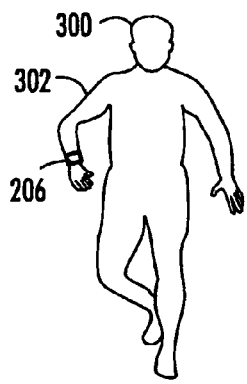
FIG. 4 illustrates determination of the physical activity level in the case of walking.

The arrangement described in FIG. 1B is part of a portable measuring device. A measuring device which measures energy consumption during exercise is described in the applicant's patent publication U.S. Publication No. 2005-0004436 A1, which is incorporated herein by reference. FIG. 3 illustrates use of a measuring device 206 in the determination of the physical activity level in the case of sitting. The person 300 subject to the determination sits at a desk and uses a computer. The measuring device 206 attached to the person's upper limb 302, to the wrist in our example, is used for measuring and analysing upper limb movements in the above described manner. In FIG. 4, the person 300 walks with the measuring device 206 attached to his/her upper limb 302, which allows determination of his/her physical activity level during walking.

In the wrist-worn measuring device, the movement sensor 114 is thus on the user's wrist where it measures hand movements. Signals arriving from the movement sensor 114 are analysed in the processing unit 100. The user's physical activity level can be recognized on the basis of upper limb movements in the above described manner. The physical activity level can be defined as different states, for example rest, standing, walking, and running. An index can be formed from the activity level, for example a 24-hour activity index.

Figure 5:
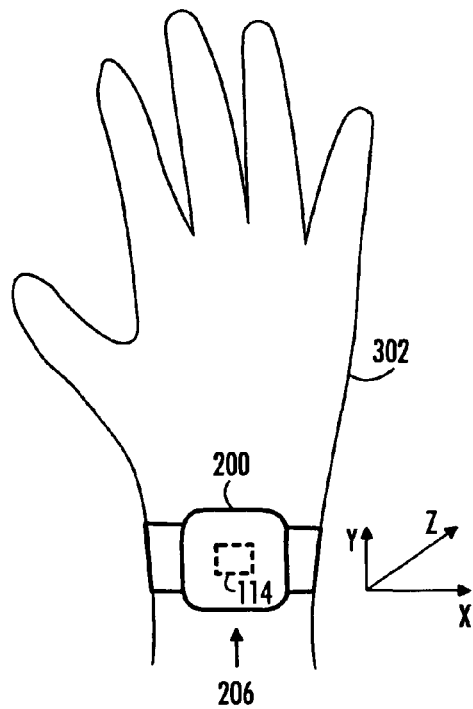
FIG. 5 illustrates the use of the arrangement in measuring different directions of movements of an upper limb.

FIG. 5 illustrates the use of the arrangement in measuring various directions of movement of an upper limb. The measuring device 206 attached to the upper limb 302 thus comprises a movement sensor 114, which is inside a cover 200 in our example. There are movement sensors 114 available with one, two and three axes. The axis refers to the measurement direction of movement. In FIG. 5, the upper limb 302 movement can thus be measured three dimensionally in the above described manner in the directions of the axes x, y and z. However, movement sensors 114 measuring the movement in the direction of one or two axes are more typical and cheaper. In an embodiment, the movement sensor 114 measures upper limb movements in one direction. If the arrangement is mounted in a wrist-worn measuring device 206, the measurement direction of the movement sensor 114 can then be the y-axis parallel with the arm or the x-axis transverse to the arm. The upper limb movement of a human being results from rotation of the shoulder joint and the elbow joint. Consequently, the movement is very complex, but as regards the present embodiments, it is sufficient to measure the upper limb movement in at least one direction. For the sake of clarity, the movement in the direction of the y-axis can be defined as longitudinal movement parallel with the dorsal plane (back of the hand) of the forearm and movement in the direction of the x-axis as movement transverse to the dorsal plane of the forearm.

In an embodiment, the movement sensor 114 comprises an acceleration sensor, which measures upper limb movements as acceleration. The acceleration sensor 114 is also known by the term 'accelerometer'. The accelerometer converts the acceleration caused by movement or gravity into an electric signal. Acceleration can be expressed by the unit of measurement g. One g is the acceleration caused to an object by the earth's gravity. Accelerations between −2 g to +2 g usually result from human movement. The movement sensor 114 can also be based on other appropriate techniques, for example on a gyroscope integrated into a silicon chip or on a micro vibration switch incorporated into a surface mounting component.

A plurality of various techniques may be used for measuring acceleration. Piezo-resistor technology employs material whose resistance changes as it compresses. The acceleration of mass produces a force in a piezo resistor. If constant current is supplied through the piezo resistor, its voltage changes according to the compression caused by acceleration. In piezo-electric technology, a piezo-electric sensor generates an electric charge when the sensor is being accelerated. In silicon bridge technology, a silicon chip is etched so that a silicon mass remains on it at the end of a silicon beam. When acceleration is directed to the silicon chip, the silicon mass focuses a force on the silicon beam, thus changing the resistance of the silicon beam. Micro-machined silicon technology is based on the use of a differential capacitor. Voice coil technology is based on the same principle as a microphone. Examples of suitable movement sensors are: Analog Devices ADXL105, Pewatron HW series devices or VTI Technologies SCA series devices.

In addition to the above-mentioned processing unit 100 and movement sensor 114, the measuring device may include a user interface 102. The user interface 102 typically consists of a display 104, a means for producing sound 106, and a keyboard 108. The display 104 may be a liquid crystal display, for example, but it can also be implemented by any appropriate prior art technique. The means 106 for producing sound may be a loudspeaker or a simpler means for producing beeps or other sound signals. The keyboard 108 may comprise a complete qwerty keyboard, a mere numeric keypad or only a few key buttons and/or rotary buttons. In addition, the user interface 102 may comprise other prior art user interface elements, for example various means for focusing a cursor (mouse, track ball, various arrow keys, etc.) or elements enabling audio control.

Figure 2:
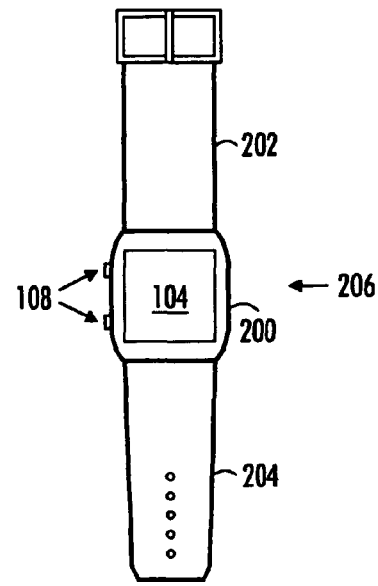
FIG. 2 illustrates an example of the appearance of the measuring device.

The measuring device may also be a sports watch for use as an instrument in sports, hiking, sailing, mountain climbing and/or in snow sports. The measuring device may include a heart rate measuring unit 112 which measures the user's heart rate. In addition to the physical activity level determined, the processing unit may take the user's measured heart rate into account in forming the user's energy consumption. Thus the measuring device illustrated in FIG. 1B may be, for example, a wrist-worn measuring device shown in FIG. 2. In the wrist-worn measuring device, the electronics components shown in FIG. 1B, such as the keys 108 shown in FIG. 2 and a liquid crystal display 104, are protected by a cover 200 (which is usually waterproof). In addition, the wrist-worn measuring device comprises a wristband 202, 204 for attaching the device to the wrist.

The device may thus be a heart rate monitor for measuring the user's heart rate, and possibly other parameters that can be measured non-invasively (such as blood pressure). In U.S. Pat. No. 4,625,733, which is incorporated herein by reference, Säynäjäkangas describes a wireless and continuous heart rate monitoring concept where a transmitter to be attached to the user's chest measures the user's ECG-accurate (electrocardiogram) heart rate and transmits the heart rate information telemetrically to the heart rate receiver attached to the user's wrist using magnetic coils in transmission. The heart rate monitor can also be implemented so that, instead of the solution consisting of a transmitter/receiver, the heart rate is measured directly from the wrist based on the pressure, for example. Other prior art methods for measuring the heart rate may also be employed, provided that they are suitable for use in a portable personal data processing device.

Polar Electro® (web pages at the address www.polar.fi) designs and manufactures heart rate monitors which comprise an electrode transmitter belt worn around the chest and an actual heart rate monitor worn on the wrist. The electronics unit in the electrode transmitter belt receives heart rate information from electrodes, which are used for measuring one or more parameters of the heart rate information. From the electrodes, the signal is transmitted to an ECG preamplifier, from which the signal is supplied to a transmitter via an AGC amplifier (Automatic Gain Control) and a power amplifier. The transmitter may be implemented as a coil, which transmits the heart rate information inductively to the receiver. For example, one burst of 5 kHz or a group of several bursts may correspond to one heartbeat. Information may be transmitted inductively or using another appropriate prior art data transmission method, for example over radio waves, optically or via a conduit. The receiver of the actual heart rate monitor can be implemented as a receiving coil, from which the received signal is transmitted via the signal receiver to the control unit 100, which controls and coordinates the function of the different components of the heart rate monitor. The heart rate monitor often comprises an interface 126 with the outside world. Information stored in the heart rate monitor can be transmitted via the interface 126 to further processing, for example to a personal computer. The software of the heart rate monitor can also be updated via the interface 126.

The measuring device also includes an independent power source 110, for example a non-chargeable battery or a chargeable battery. A solar cell, which generates energy from a light source and is either connected to the device or integrated into it, may also be utilized for obtaining power. Other prior art methods of generating power for a portable device may also be employed, such as a small-size generator, which produces power from movement and has been developed by watch producer Seiko®.

The processing unit 100 is usually implemented as a processor with software, but various hardware implementations are also feasible, such as a circuit consisting of logic components or one or more application-specific integrated circuits (ASIC). The processor may be, for example, an 8-bit microprocessor, type S1C8F manufactured by Seiko-Epson®. If necessary, there may be more than one processor. A hybrid of these implementations is also feasible. In selecting the implementation, a person skilled in the art will pay attention to the requirements set for the size and power consumption of the device, the required processing capacity and the production costs and volumes.

Part of the functionality of the processing unit can thus be implemented as a computer program. For its distribution, the computer program can be stored in a computer program distribution medium. The computer program distribution medium is readable by a data processing device and it encodes computer program commands to enable the running of a computer process which determines the physical activity level of a human being. The process comprises: receiving measured upper limb movements of the human being; filtering upper limb movements following one another more frequently than a predetermined threshold period from the upper limb movements during a determination period; forming the number of upper limb movements during the determination period from the filtered upper limb movements during the determination period; and determining the physical activity level on the basis of the number of upper limb movements during the determination period formed from the filtered upper limb movements during the determination period. The computer program can thus implement the processing blocks 116, 118, 120, 122, 124 of FIG. 1A. The distribution medium may be any prior art solution for distributing a computer program, for example a medium readable by a data processing device, a software distribution package readable by a data processing device, a signal readable by a data processing device, a telecommunication signal readable by a data processing device, and a compressed software package readable by a data processing device.

In an embodiment, a predetermined threshold period in the processing unit 100 includes periods longer than 0.4 seconds but shorter than 1.0 seconds. The purpose is to concentrate on movement frequencies typical of a human body (1 to 2 movements per second). This is implemented by rejecting very short movement intervals. In the processing unit 100, the predetermined threshold period may be a period with a length of 0.6 seconds. This corresponds to 100 movements per minute.

In an embodiment, the processing unit 100 further recognizes filtered upper limb movements as a rhythmic activity if a number of intervals between subsequent filtered movements according to a predetermined number threshold value are equal with the accuracy of a predetermined variation threshold value. The processing unit employs the recognized rhythmic activity in the determination of the physical activity level. Rhythmic activities are thus recognized on the basis of the fact that during them, a majority of movement intervals are equal to a previous movement interval within the selected range of variation. It is advantageous to test rhythmicity after very short movement intervals, e.g. those with a length less than 0.6 seconds as described above, have been filtered out. In the processing unit 100, the predetermined number threshold value may be 65 to 95% of the total number of intervals and the predetermined variation threshold value may be ±10-30% of the average interval length. In an embodiment, the predetermined number threshold value in the processing unit 100 is 75% of the total number of intervals and the predetermined variation threshold value is ±25% of the average interval length.

In an embodiment, the processing unit 100 further filters upper limb movements following one another more frequently than a predetermined extended threshold period from the filtered upper limb movements if the processing unit 100 did not recognize filtered upper limb movements as a rhythmic activity. The unit also uses the doubly filtered upper limb movements in forming the number of movements and in determining the physical activity level. In an embodiment, the extended threshold period in the processing unit 100 includes periods longer than 0.7 seconds but shorter than 1.2 seconds. In an embodiment, the predetermined threshold period in the processing unit 100 may be a period with a length of 0.85 seconds. This efficiently limits the influence of irregular pulse intervals in the case of typical activities with an average activity level. Thanks to this second filtering, high pulse frequencies related to high energy consumption can be achieved only at regular intervals.

Figure 6:
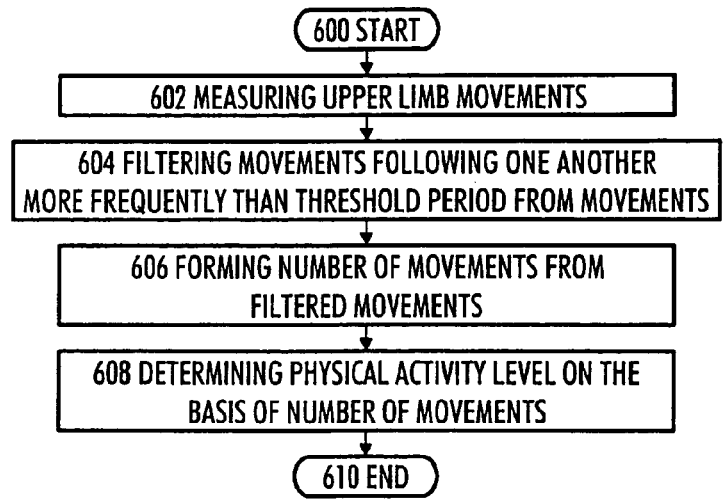
FIG. 6 is a flow chart illustrating a method of determining the physical activity level of a human being.

In the following, the method of determining the physical activity level of a human being will be described with reference to FIG. 6. The method starts in 600, for example when the function for determining the physical activity level is started by means of the user interface of the above described measuring device.

Then in 602, upper limb movements of the human being are measured in the manner described above, for instance. Next in 604, upper limb movements following one another more frequently than the predetermined threshold period are filtered from upper limb movements during the determination period, and in 606, the number of upper limb movements during the determination period is formed from the filtered upper limb movements during the determination period. In an embodiment, the filtering 604 is performed by rejecting the movements following each accepted upper limb movement and measured during the predetermined threshold period.

Finally in 608, the physical activity level is determined from the number of upper limb movements during the determination period formed from the filtered upper limb movements during the determination period. The method ends in 610, where the function for determining the physical activity level is switched off by means of the user interface of the measuring device, for example. It should be noted that operations 602, 604, 606, 608 are repeated as long as one wishes to continue the determination of the physical activity level. In other words, this is an operation which expresses the physical activity level of a human being as a function of time.

In an embodiment, the predetermined threshold period includes periods longer than 0.4 seconds but shorter than 1.0 seconds. The predetermined threshold period may be a period with a length of 0.6 seconds.

Figure 7:
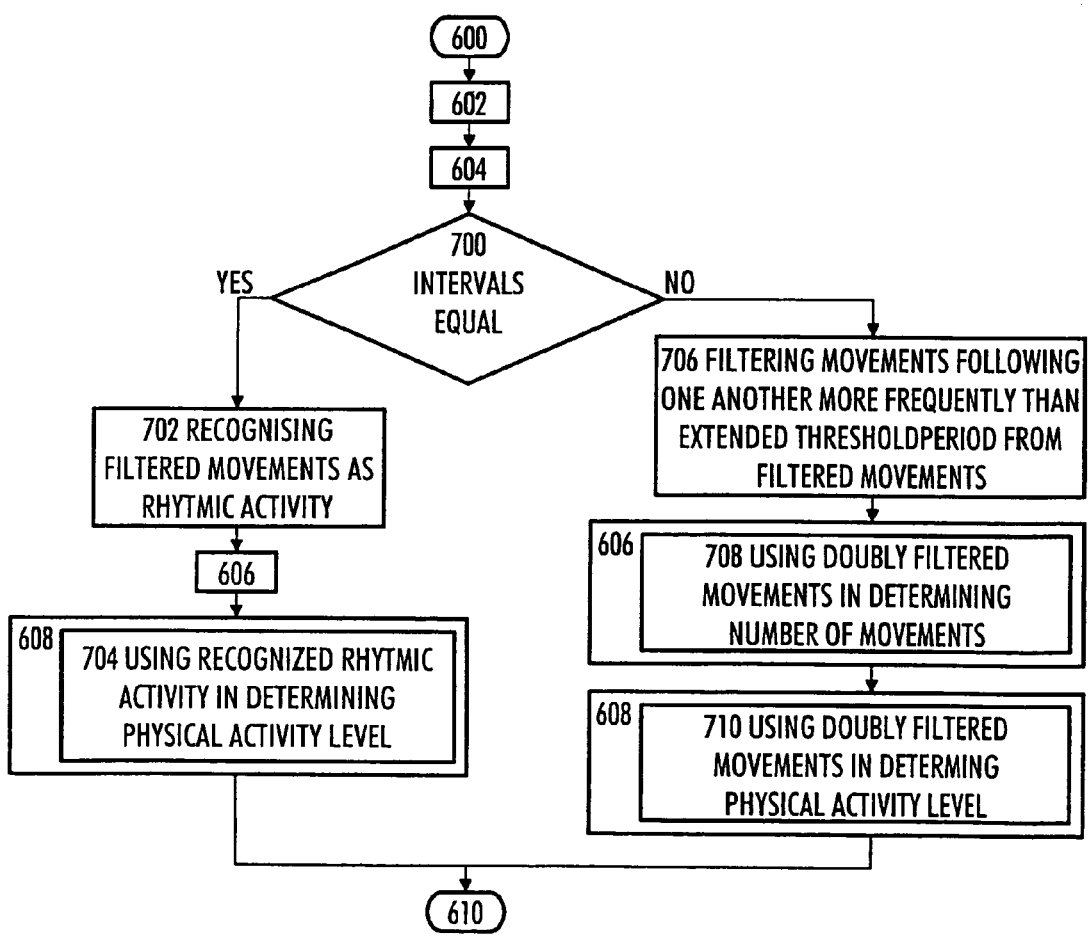
FIG. 7 is a flow chart illustrating embodiments of the method.

Embodiments of the method will be examined with reference to FIG. 7. First, operations 600, 602 and 604 are performed as described above. The in 700, the intervals between subsequent filtered movements are compared with one another.

If a number of intervals between filtered subsequent movements according to a predetermined number threshold value are equal with the accuracy of a predetermined variation threshold value, the process continues to 702, where the filtered upper limb movements are recognized as a rhythmic activity. After this, in operation 606, the number of upper limb movements during the determination period is formed from the filtered upper limb movements during the determination period. Finally in 608, the physical activity level is determined from the number of upper limb movements during the determination period formed from the filtered upper limb movements during the determination period. In addition, 704 employs a recognized rhythmic activity in accordance with 608 in the determination of the physical activity level. In an embodiment, the predetermined number threshold value includes 65 to 95% of the total number of intervals and the predetermined variation threshold value includes ±10 to 30% of the average interval length. In an embodiment, the predetermined number threshold value may be 75% of the total number of intervals and the predetermined variation threshold value may be ±25% of the average interval length.

If the filtered upper limb movements were not recognized as a rhythmic activity in 700, the process continues to 706, where upper limb movements following one another more frequently than the predetermined extended threshold period are filtered from the filtered upper limb movements. After that, in accordance with 708 and 710, the doubly filtered upper limb movements are used in forming the movements and the number in 606 and in determining the physical activity level in 608. In an embodiment, the predetermined extended threshold period includes periods longer than 0.7 seconds but shorter than 1.0 seconds. In an embodiment, the predetermined extended threshold period may be a period with a length of 0.85 seconds.

The method can be implemented by a measuring device described above, which may be, for example, part of a measuring device which measures energy consumption, such as a heart rate monitor, but a person skilled in the art may also apply the above described method to other kinds of devices intended for determining the physical activity level of a human being. In an embodiment, upper limb movements of a human being are measured by a movement sensor attached to an upper limb as described above. In an embodiment, upper limb movements are measured as acceleration. In an embodiment, upper limb movements are measured in one direction. In an embodiment, the measuring of upper limb movements comprises measuring longitudinal movements parallel with the dorsal plane of the forearm and/or movements transverse to the dorsal plane of the forearm.

In the following, tests carried out by the applicant will be described with reference to FIGS. 8, 9, 10, 11 and 12. Five testees took a controlled test including eight tasks: working on a personal computer, sweeping the floor, moving items on shelves, walking at rates of 3, 5 and 7 km/h and running at rates of 7 and 10 km/h. The horizontal axes in the figures represent the passing of time in minutes as the testees switched from one task to another. The vertical axes in the figures represent the number of upper limb movements. The testees were wearing two movement sensors on their wrists, one of which recognized movements parallel with the arm and the other trans-verse movements. Swings of the arm were recognized from the measured analogue signal on the basis of exceeding of the threshold value. The threshold value used corresponded approximately to acceleration of 0.05 g.

Figure 8:
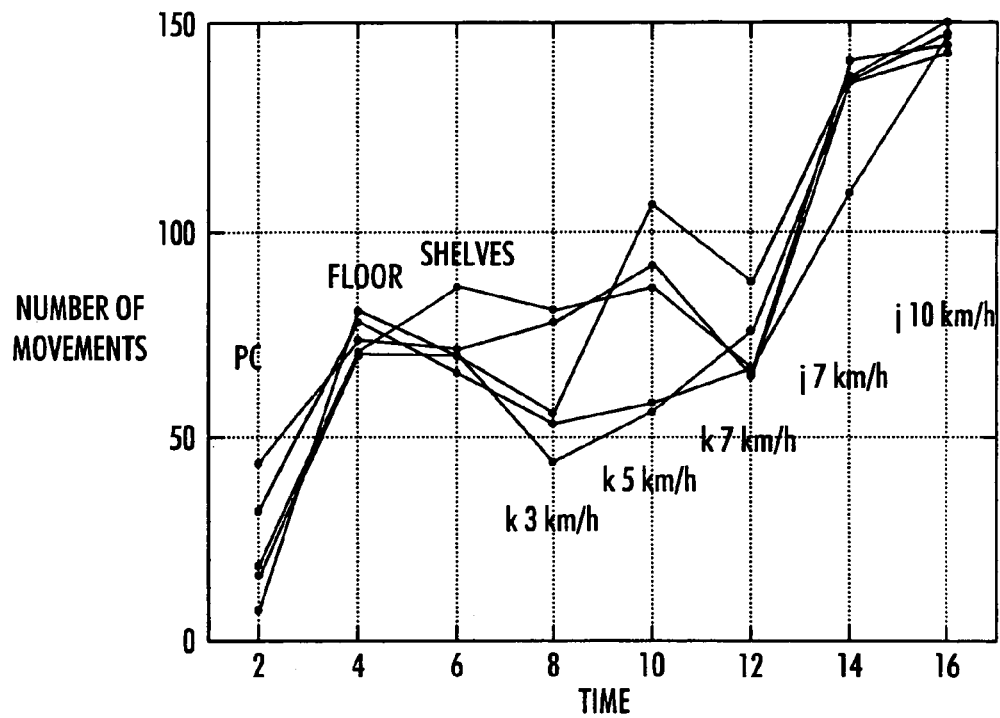
FIGS. 8, 9, 10, 11, 12 and 13 illustrate tests carried out by the applicant.
Figure 9:
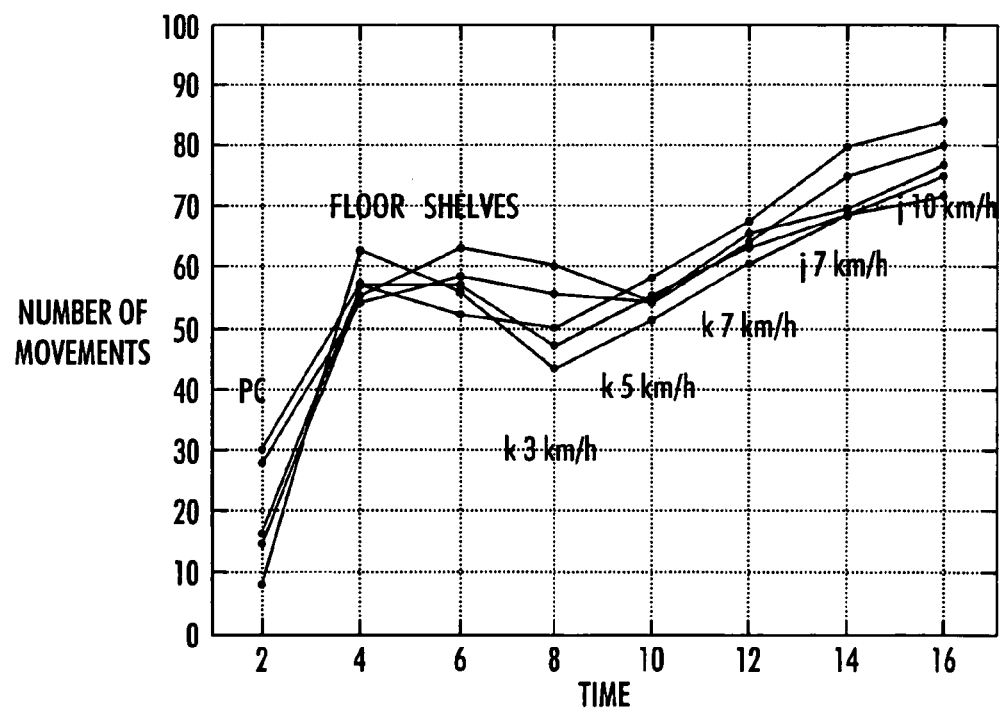
Figure 10:
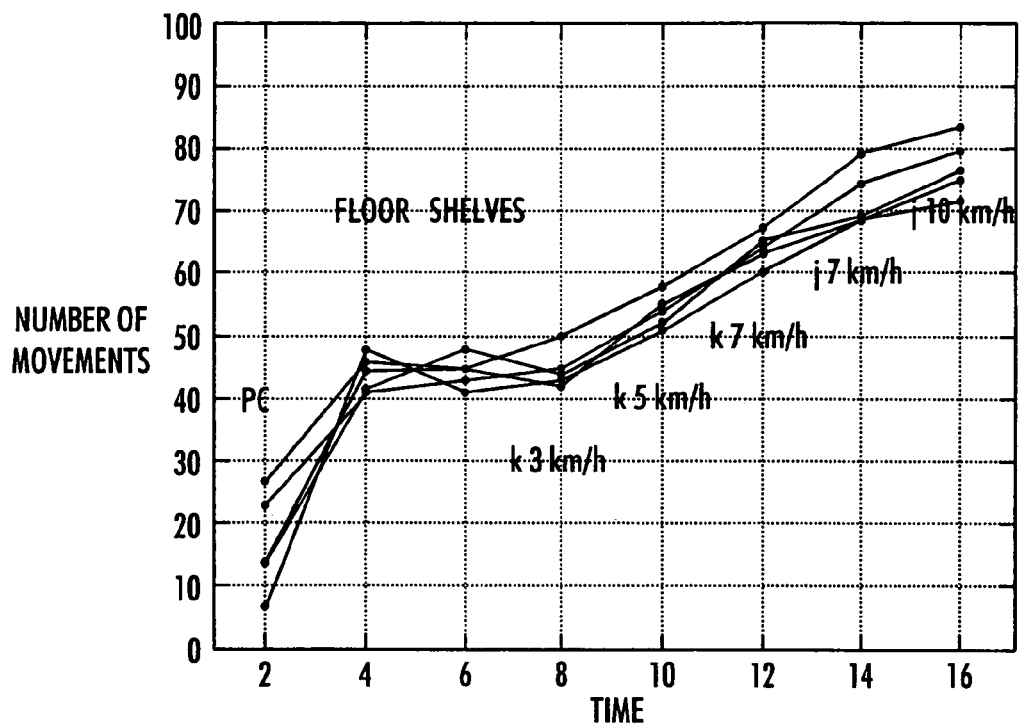
Figure 11:
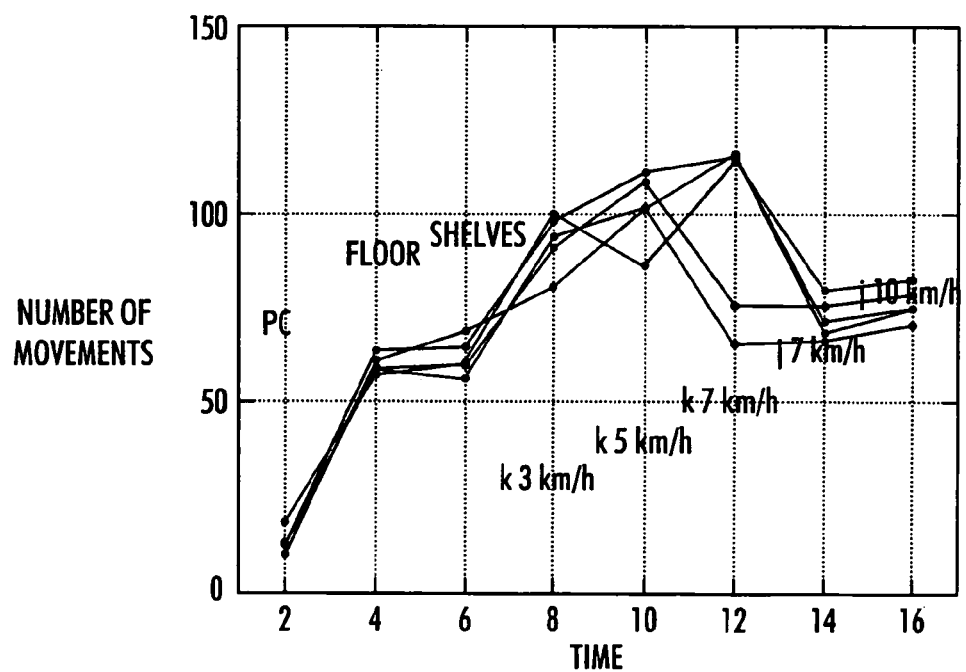
Figure 12:
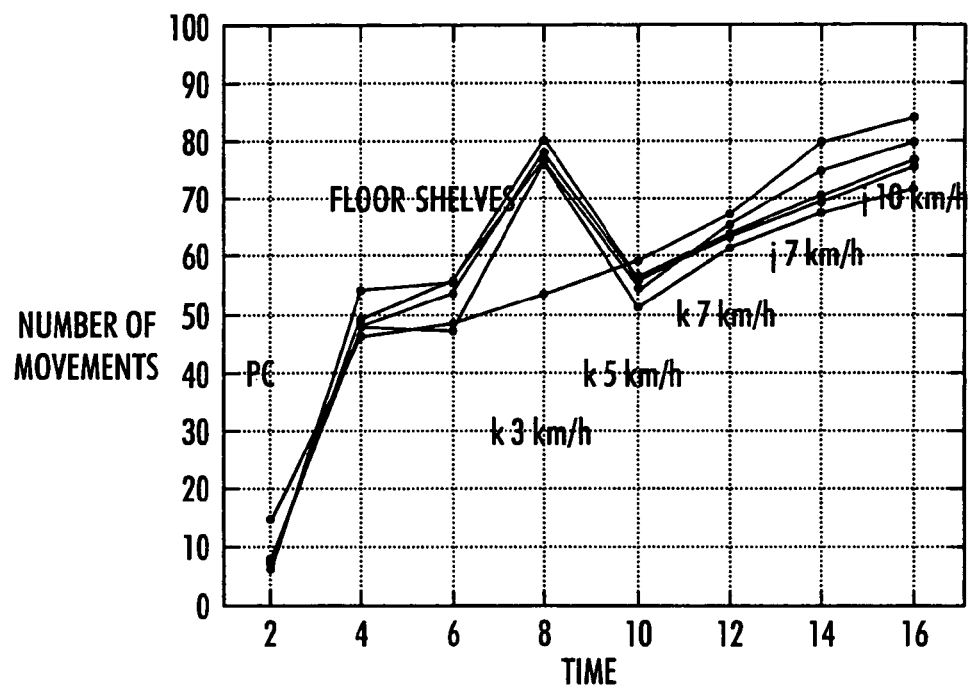
Figure 13:
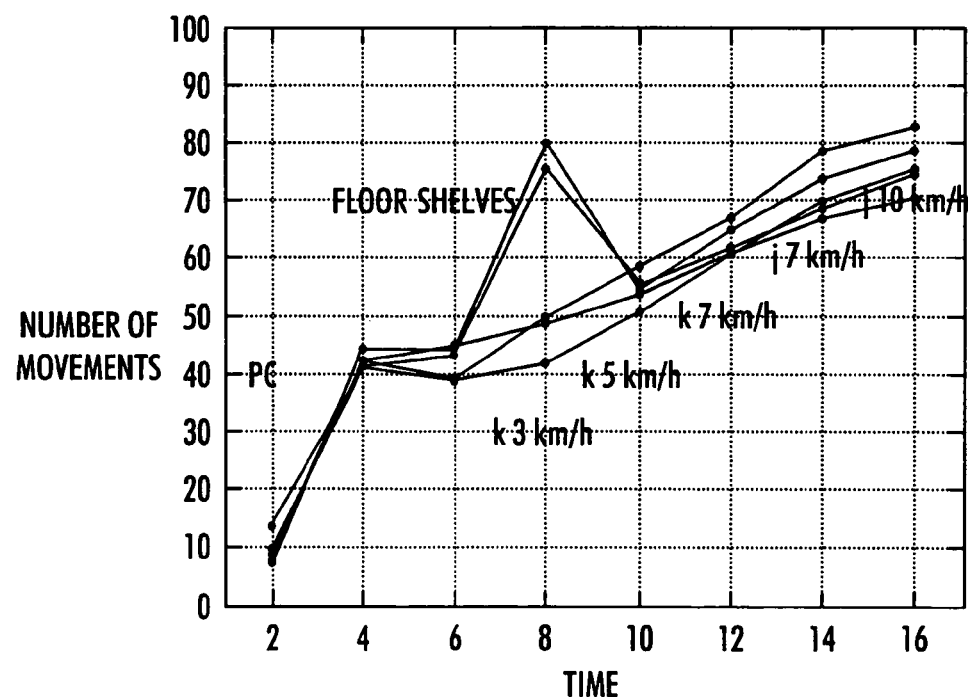

FIGS. 8, 9 and 10 illustrate results measured by sensors recognizing movements parallel with the arm before filtering operations and after them. FIGS. 11, 12 and 13 show corresponding measurement results measured by a sensor recognizing movements transverse to the arm.

FIGS. 8 and 11 clearly show the problems that occur when the measured movements are not filtered at all: the numbers of movements measured for different persons vary a lot at all walking rates; the numbers of movements measured for standing work and light chores are the same as those measured for brisk walking, and too large numbers of movements were measured for a small number of testees in sedentary work.

FIGS. 9 and 12 illustrate results when movements following one another more frequently than 0.6 seconds are filtered out. The problems solved are: the numbers of movements measured for different persons do not vary in normal or brisk walking, and too large numbers of movements are not obtained for working on a personal computer. The following problems remained in this test arrangement: the numbers of movements measured for different persons still vary slightly in slow walking, and equally large numbers of movements are still measured for standing work and light chores and for brisk walking.

FIGS. 10 and 13 illustrate the results after rhythmic activities had been recognized from filtered movements and a second filtering had been performed, where movements following one another more frequently than 0.85 seconds in rhythmic activities had been filtered out. The problems solved are: the numbers of movements measured for different persons hardly vary at all at any walking rate (the variation in the height of the persons explains remaining variation) and in standing work and light chores frequencies of movement corresponding to slow walking and with a correct level of energy consumption are measured. Furthermore, the comparison of FIGS. 10 and 13 shows that using the presented post-processing, nearly equal numbers of movements are achieved by the sensors recognizing movements in different directions.

Even though the invention was described above with reference to an example according to the accompanying drawings, it is clear that the invention is not restricted to it, but the invention may be modified in various ways within the scope of the attached claims.

What is claimed is:

1. An arrangement for determining the physical activity level of a human being, the arrangement comprising:
a movement sensor capable of being attached to an upper limb of the human being for measuring upper limb movements; and
a processing unit connected to the movement sensor for filtering the upper limb movements during a determination period such that the upper limb movements measured during a predetermined threshold period following each accepted upper limb movement are rejected from the accepted upper limb movements, for forming the number of filtered upper limb movements during the determination period from the number of accepted upper limb movements during the determination period, for determining the physical activity level on the basis of the number of filtered upper limb movements during the determination period, and for recognizing filtered upper limb movements as a rhythmic activity if a number of intervals between subsequent filtered movements according to a predetermined number threshold value are equal with the accuracy of a predetermined variation threshold value and using the recognized rhythmic action in determining the physical activity level, wherein the processing unit is further configured to filter the filtered upper limb movements following one another more frequently than an extended threshold period if the processing unit did not recognize the filtered upper limb movements as a rhythmic activity and to use the doubly filtered upper limb movements in forming the number of movements and in determining the physical activity level.

2. An arrangement according to claim 1, wherein the predetermined threshold period in the processing unit includes periods longer than 0.4 seconds but shorter than 1.0 seconds.

3. An arrangement according to claim 1, wherein the predetermined threshold period in the processing unit includes a period with a length of 0.6 seconds.

4. An arrangement according to claim 1, wherein the predetermined number threshold value in the processing unit comprises 65 to 95% of the total number of intervals and the predetermined variation threshold value comprises ±10 to 30% of the average interval length.

5. An arrangement according to claim 1, wherein the predetermined number threshold value in the processing unit comprises 75% of the total number of intervals and the predetermined variation threshold value comprises ±25% of the average interval length.

6. An arrangement according to claim 1, wherein the predetermined extended threshold period in the processing unit comprises periods longer than 0.7 seconds but shorter than 1.2 seconds.

7. An arrangement according to claim 1, wherein the predetermined extended threshold period in the processing unit comprises a period with a length of 0.85 seconds.

8. An arrangement according to claim 1, wherein the movement sensor comprises an acceleration sensor that is configured to measure upper limb movements as acceleration.

9. An arrangement according to claim 1, wherein the movement sensor is configured to measure upper limb movements in one direction.

10. An arrangement according to claim 1, wherein the movement sensor is configured to measure upper limb movements as longitudinal movements parallel with the dorsal plane of the forearm and/or as movements transverse to the dorsal plane of the forearm.

11. An arrangement according to claim 1, wherein the arrangement is part of a measuring device configured to measure energy consumption involved in exercise.

12. A method of determining the physical activity level of a human being, the method comprising:
measuring upper limb movements of the human being;
filtering, using a processing device, the upper limb movements during a determination period such that the upper limb movements measured during a predetermined threshold period following each accepted upper limb movement are rejected from the accepted upper limb movements;
forming, using the processing device, the number of filtered upper limb movements during the determination period from the number of accepted upper limb movements during the determination period;
determining, using the processing device, the physical activity level on the basis of the number of filtered upper limb movements during the determination period;
providing user access to the physical activity level;
recognizing filtered upper limb movements as a rhythmic activity if a number of intervals between subsequent filtered movements according to a predetermined number threshold value are equal with the accuracy of a predetermined variation threshold value;
using the rhythmic activity in determining the physical activity level;
filtering the filtered upper limb movements following one another more frequently than an extended threshold period if the filtered upper limb movements were not recognized as a rhythmic activity; and
using the doubly filtered upper limb movements in forming the number of movements and in determining the physical activity level.

13. A method according to claim 12, wherein the predetermined threshold period comprises periods longer than 0.4 seconds but shorter than 1.0 seconds.

14. A method according to claim 12, wherein the predetermined threshold period includes a period with a length of 0.6 seconds.

15. A method according to claim 12, wherein the predetermined number threshold value comprises 65 to 95% of the total number of intervals and the predetermined variation threshold value comprises ±10 to 30% of the average interval length.

16. A method according to claim 12, wherein the predetermined number threshold value comprises 75% of the total number of intervals and the predetermined variation threshold value comprises ±25% of the average interval length.

17. A method according to claim 12, wherein the predetermined extended threshold period comprises periods longer than 0.7 seconds but shorter than 1.2 seconds.

18. A method according to claim 12, wherein the predetermined extended threshold period comprises a period with a length of 0.85 seconds.

19. A method according to claim 12, the method further comprising measuring upper limb movements of the human being by a movement sensor attached to an upper limb.

20. A method according to claim 12, the method further comprising measuring upper limb movements as acceleration.

21. A method according to claim 12, the method further comprising measuring upper limb movements in one direction.

22. A method according to claim 12, the method further comprising measuring upper limb movements by measuring longitudinal movements parallel with the dorsal plane of the forearm and/or movements transverse to the dorsal plane of the forearm.

23. An arrangement for determining the physical activity level of a human being, the arrangement comprising:
movement measuring means for measuring upper limb movements, the movement measuring means for measuring upper limb movements capable of being attached to an upper limb of the human being; and
processing means for filtering the upper limb movements during a determination period such that the upper limb movements measured during a predetermined threshold period following each accepted upper limb movement are rejected from the accepted upper limb movements, for forming the number of filtered upper limb movements during the determination period from the number of accepted upper limb movements, for determining the physical activity level on the basis of the number of filtered upper limb movements during the determination period, and for recognizing filtered upper limb movements as a rhythmic activity if a number of intervals between subsequent filtered movements according to a predetermined number threshold value are equal with the accuracy of a predetermined variation threshold value and using the recognized rhythmic activity in determining the physical activity level, wherein the processing means is further configured to filter the filtered upper limb movements following one another more frequently than an extended threshold period if the processing means did not recognize the filtered upper limb movements as a rhythmic activity and to use the doubly filtered upper limb movements in forming the number of movements and in determining the physical activity level.

24. A non-transitory computer-readable distribution medium comprising computer program instructions stored thereon configured to cause a data processing device to determine the physical activity level of a human being by:
receiving measured upper limb movements of the human being;
filtering the upper limb movements during a determination period such that the upper limb movements measured during a predetermined threshold period following each accepted upper limb movement are rejected from the accepted upper limb movements;
forming the number of filtered upper limb movements during the determination period from the number of accepted upper limb movements during the determination period;
determining the physical activity level on the basis of the number of filtered upper limb movements during the determination period;
recognizing filtered upper limb movements as a rhythmic activity if a number of intervals between subsequent filtered movements according to a predetermined number threshold value are equal with the accuracy of a predetermined variation threshold value;
using the rhythmic activity in determining the physical activity level;
filtering the filtered upper limb movements following one another more frequently than an extended threshold period if the filtered upper limb movements were not recognized as a rhythmic activity; and
using the doubly filtered upper limb movements in forming the number of movements and in determining the physical activity level.

25. A non-transitory computer-readable distribution medium according to claim 24, wherein the medium comprises at least one of a medium readable by the data processing device, a program storage medium, a storage medium, a memory readable by the data processing device, a software distribution package readable by the data processing device, information readable by the data processing device, and a compressed software package readable by the data processing device.

* * * * *